(12) United States Patent
Barnard et al.

(10) Patent No.: US 6,676,605 B2
(45) Date of Patent: Jan. 13, 2004

(54) BLADDER WALL THICKNESS MEASUREMENT SYSTEM AND METHODS

(75) Inventors: Bill Barnard, Woodinville, WA (US); Stephen Dudycha, Kirkland, WA (US)

(73) Assignee: Diagnostic Ultrasound, Woodinville, WA (US)

( * ) Notice: Subject to any disclaimer, the term of this patent is extended or adjusted under 35 U.S.C. 154(b) by 0 days.

(21) Appl. No.: 10/165,556

(22) Filed: Jun. 7, 2002

(65) Prior Publication Data

US 2003/0229281 A1 Dec. 11, 2003

(51) Int. Cl.[7] .................................................. A61B 8/02
(52) U.S. Cl. ........................................................ 600/449
(58) Field of Search ................................ 600/300–471, 600/481–587; 382/128, 131, 276; 128/898, 916; 606/1, 7, 12, 15, 17, 48; 604/6.08, 394; 601/2, 3; 367/7, 11, 103, 105; 73/625, 626

(56) References Cited

U.S. PATENT DOCUMENTS

| | | | | |
|---|---|---|---|---|
| 5,235,985 A | * | 8/1993 | McMorrow et al. | 600/443 |
| 5,698,549 A | * | 12/1997 | Steers et al. | 514/211.07 |
| 5,908,390 A | * | 6/1999 | Matsushima | 600/447 |
| 5,964,710 A | * | 10/1999 | Ganguly et al. | 600/449 |
| 6,213,949 B1 | * | 4/2001 | Ganguly et al. | 600/449 |

OTHER PUBLICATIONS

Matthews et al., "The Use of Ultrasound in the Investigation of Prostatism," British Journal of Urology, 54, 1982, pp. 536–538, 1982 British Association of Urological Surgeons.
Cascione et al., "Transabdominal Ultrasound Versus Excretory Urography in Preoperative Evaluation of Patients with Prostatism," The Journal of Urology, May 18–22, 1986, pp. 883–885, vol. 137. The Williams & Wilkins Co., USA.
Christensen et al., Clinical Manifestations of Benign Prostatic Hyperplasia and Indications for Therapeutic Intervention, Urologic Clinics of North America, Aug. 3, 1990, pp. 509–516, vol. 17.
Madsen et al., "Clinical Manifestations of Benign Prostatic Hyperplasia," Urologic Clinics of North America, vol. 22, No. 2, pp. 291–298, May 1995.
Kojima et al., "Ultrasonic Estimation of Bladder Weight as a Measure of Bladder Hypertrophy in Men with Infravesical Obstruction: A Preliminary Report," 1996, pp. 942–947, Elsevier Science Inc.
Boyle et al., "Prostate Volume Predicts Outcome of Treatment of Benign Prostatic Hyperplasia with Finasteride: Meta–analysis of Randomized Clinical Trials", 1996, pp. 398–406, Elsevier Science Inc.
Khullar et al., "Ultrasound: a Noninvasive Screening Test for Detrusor Instability," British Journal of Obstetrics and Gynaecology, Sep. 1996, pp. 904–908, vol. 103.
Barentsz et al., Primary Staging of Urinary Bladder Carcinoma: the role of MRI and a comparison with CT, Edr. Radiol., 1996, pp. 129–133, vol. 6.
Miyashita et al., "Ultrasonic Measurement of Bladder Weight as a Possible Predictor of Acute Urinary Retention in Men with Lower Urinary Tract Symptoms Suggestive of Benign Prostatic Hyperplasia," Ultrasound in Medicine and Biology, 2002, pp. 985–990, vol. 28 No. 8.
Gerald, et al., "Applied Numerical Analysis," Fifth Edition, California Polytechnic State University, Addison–Wesley Publishing Company, Reading, MA.
Scheinerman, "Invitation to Dynamical Systems," Department of Mathematical Sciences, The Johns Hopkins University, Prentice Hall, Upper Saddle River, NJ.

* cited by examiner

Primary Examiner—Ali M. Imam
(74) Attorney, Agent, or Firm—Black Lowe & Graham, PLLC (57) ABSTRACT

An ultrasound transceiver scans a bladder in a three dimensional array to measure the thickness and surface area of the bladder to determine bladder mass. The bladder wall thickness and masses may be determined for anterior, posterior, and lateral locations of the bladder.

21 Claims, 4 Drawing Sheets

BLADDER WALL THICKNESS MEASUREMENT SYSTEM AND METHODS

FIELD OF THE INVENTION

This invention relates generally to ultrasound application in diagnosing bladder dysfunction.

BACKGROUND OF THE INVENTION

A variety of techniques have been used to evaluate bladder dysfunction. Such techniques typically attempt to determine the size of the bladder or bladder volume, meaning the amount of urine in the bladder. As one example, U.S. Pat. No. 6,110,111 to Barnard discloses a system for assessing bladder distension by using ultrasound to compare the bladder surface area with the surface area of a sphere. According to Barnard, the closer the bladder is to a spherical shape, the greater the pressure within the bladder.

Bladder mass measurements can also be used to diagnose several different clinical conditions. Bladder wall thickness and bladder mass can be used to indicate bladder outlet obstruction and bladder distension. An outlet obstruction will cause a higher pressure in the urine, against which the bladder muscle must contract. That higher pressure causes the muscle to exert more force, resulting in hypertrophy of the bladder muscle. Symptoms of bladder muscle hypertrophy include increased wall thickness and increased mass. The use of bladder wall thickness as an indicator of detruser hypertrophy has been noted for many years (see Matthews P N, Quayle J B, Joseph A E A, Williams J E, Wilkinson K W, Riddle P R, The use of ultrasound in the investigation of prostatism, *British Journal of Urology*, 54:536–538, 1982; and Cascione C J, Bartone F F, Hussain M B, Transabdominal ultrasound versus excretory urography in preoperative evaluation of patients with prostatism, *Journal of Urology*, 137:883–885, 1987). Converting bladder wall thickness to bladder wall volume (or bladder mass by multiplying bladder wall volume by the specific gravity of bladder tissue) yields a single number, which is independent of bladder volume. While the bladder wall thins as volume increases, the total bladder wall volume (or bladder mass) remains unchanged.

Another key parameter of bladder functionality is bladder distension. As the bladder volume and bladder pressure increases, the bladder walls stretch and thin. Two prominent maladies associated with bladder distension are incontinence and hyperdistension.

Incontinent episodes frequently occur if the bladder sphincter muscles are unable to retain urine as bladder pressure and bladder distension increases. In many individuals this incontinent point occurs at a consistent volume. Consequently, if this volume is known and if the bladder volume can be measured over time, then incontinent events can be prevented. Furthermore, research has shown that it is possible to increase both the bladder capacity and the bladder volume incontinent point through a variety of methods. This technique has been used effectively on enuretic patients.

Hyperdistension refers to the case in which the bladder is allowed to fill to such an extreme that excessive bladder pressure builds which can cause potential renal damage, renal failure and even patient death from autonomic dysreflexia if the patient has spinal cord damage. As with incontinence, hyperdistension has been successfully prevented using non-invasive bladder volume measuring.

At small bladder volumes, bladder response is quite constant across humanity. Normal adult humans typically have no trouble voiding and leaving less than 50 ml of urine. Thus it has been relatively easy to establish post-void-residual (PVR) volumes that are normal and PVR volumes that are potential medical problems. At low bladder volumes bladder distension information is not as useful. However, normal humans have widely variant bladder capacities. Thus it is more difficult to establish a volume threshold at which over-distension occurs or when incontinence occurs. As the bladder fills, quantization of bladder distension becomes more useful. This is especially true since it is thought that a bladder distension metric would better indicate hyperdistension and bladder capacity.

Current methods to measure bladder wall thickness rely on one-dimensional (A-mode) and two-dimensional (B-mode) ultrasound and are greatly susceptible to operator error, time consuming, and inaccurate. The operator using one or two-dimensional ultrasound has to repeatedly reposition the ultrasound probe until a bladder wall image is sufficiently visible, usually the more anterior portion of the bladder. Furthermore, the limitations of one and two-dimensional ultrasound require inaccurate spherical model assumptions for the bladder. Presumably for these and other reasons the industry has concluded that measuring bladder wall thickness is an unreliable or ineffective means to quantize bladder distension. See, e.g., Barnard, U.S. Pat. No. 6,110,111 at column 1, lines 50–59.

Thus, there is a need for a system to accurately measure bladder wall thickness for use in evaluating bladder distension.

SUMMARY OF THE INVENTION

The present invention incorporates a three-dimensional ultrasound device to scan a patient's bladder. Data collected in the ultrasound scan are then analyzed to calculate bladder mass. Bladder mass information is then used to assess bladder dysfunction.

In accordance with the preferred embodiment of the invention, a microprocessor-based ultrasound apparatus, placed on the exterior of a patient, scans the bladder of the patient in multiple planes with ultrasound pulses, receives reflected echoes along each plane, transforms the echoes to analog signals, converts the analog signals to digital signals, and downloads to the digital signals to a computer system.

Although a variety of scanning and analysis methods may be suitable in accordance with this invention, in a preferred embodiment the computer system performs scan conversion on the downloaded digital signals to obtain a three-dimensional, conically shaped image of a portion of the bladder from mathematical analysis of echoes reflecting from the inner (submucosal) and outer (subserosal) surfaces of the bladder wall. The conical image is obtained via three-dimensional C-mode ultrasound pulse echoing using radio frequency (RF) ultrasound (approximately 3–10 MHz) to obtain a regularly spaced array of multiple scanplanes, each scanplane including regularly spaced multiple scanlines. The combination of regularly spaced scanplanes results in a solid angle scan cone that provides a basis to locate bladder wall regions or surface patches of the inner and outer surfaces of the bladder wall. The location of each surface patch is determined using fractal analytical methods and the distance or thickness between the inner and outer surface patches is measured. The bladder wall mass is calculated as a product of the surface area of the bladder, the bladder wall thickness, and the specific gravity of the bladder wall. The entire bladder wall or various regions, including anterior, posterior, and lateral portions of the bladder, may be measured for thickness and mass.

An alternate embodiment of the invention configures the downloaded digital signals to be compatible with a remote microprocessor apparatus controlled by an Internet web-based system. The Internet web-based system has multiple programs that collect, analyze, and store organ thickness and organ mass determinations. The alternate embodiment thus provides an ability to measure the rate at which internal organs undergo hypertrophy with time. Furthermore, the programs include instructions to permit disease tracking, disease progression, and provide educational instructions to patients.

BRIEF DESCRIPTION OF THE DRAWINGS

The preferred and alternative embodiments of the present invention are described in detail below with reference to the following drawings.

DETAILED DESCRIPTION OF THE INVENTION

Figure 1:
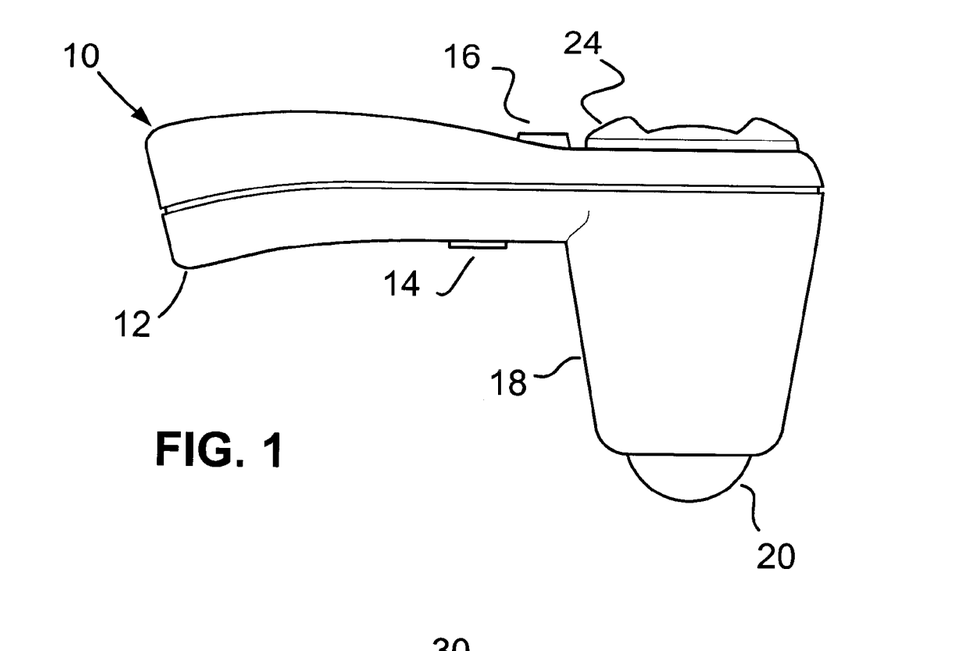
FIG. 1 is a microprocessor-controlled transceiver.

The portable embodiment of the ultrasound transceiver of the present invention is shown in FIG. 1. The transceiver 10 includes a handle 12 having a trigger 14 and a gender changer 16, a transceiver housing 18 attached to the handle 12, a transceiver dome 20 and a display 24 for user interaction, attached to the transceiver housing 18 at an end opposite the transceiver dome 20. The transceiver 10 is held in position against the body of a patient by a user. In operation, the transceiver transmits a radio frequency ultrasound signal within the 3 to 10 MHz range to the body and then receives a returning echo signal. The gender changer 16 serves to adjust the delivery and reception of radio frequency ultrasound to the anatomy of a male patient and to the anatomy of a female patient. The transceiver is controlled by a microprocessor and software associated with the microprocessor and a digital signal processor of a computer system. As used in this invention, the term "computer system" broadly comprises any microprocessor-based or other computer system capable of executing operating instructions and manipulating data, and is not limited to a traditional desktop or notebook computer. The display 24 presents alphanumeric data indicating the proper or optimal positioning of the transceiver 10 for initiating a series of scans. In alternate embodiments, the two- or three-dimensional image of a scanplane may be presented in the display 24 of FIG. 1.

Although the preferred ultrasound transceiver is described above and depicted in FIG. 1, other transceivers may also be used. For example, the transceiver need not be battery-operated or otherwise portable, need not have a top-mounted display 24, and may include many other features or differences. The transceiver 10 need only be able to non-invasively probe within the body to gather data that can be used to analyze internal objects such as the bladder. The display 24 may be a liquid crystal display (LCD), a light emitting diode (LED), a cathode ray tube (CRT), or any suitable display capable of presenting alphanumeric data or graphic images.

Figure 2:
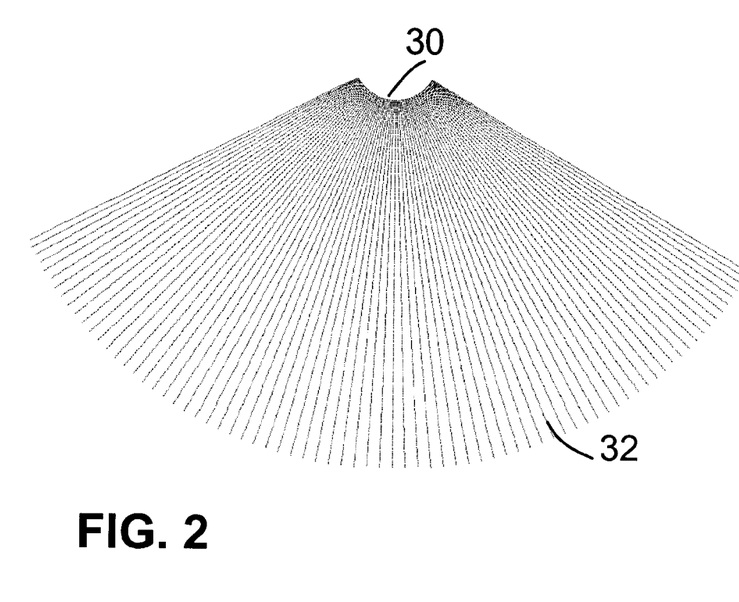
FIG. 2 is a representation of scanlines sharing a common rotational angle to form a plane.

Once optimally positioned over the abdomen for scanning, the transceiver 10 transmits an ultrasound signal (approximately 3.7 MHz in the preferred embodiment) into the bladder region. The ultrasound signal is in the form of generally linear signal bursts known as scanlines, as illustrated in FIG. 2. The scanlines, each approximately 20 cm long, originate from the transceiver dome 20, producing a dome cutout 30 in a cluster of scanlines forming a scanplane 32. Within the scanplane 32 are a plurality of scanlines that share a common rotational angle ($\theta$), but have a unique tilt angle ($\phi$). In the preferred embodiment, each plane contains 77 scan lines, although the number of lines can vary within the scope of this invention.

Figure 3:
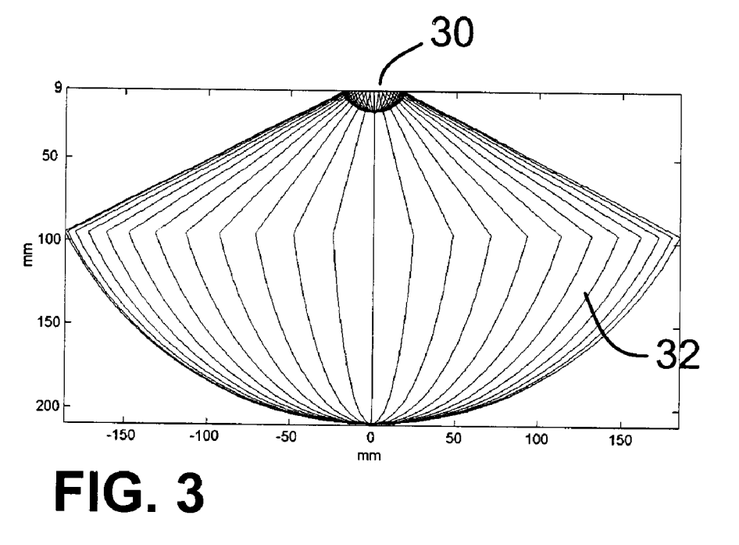
FIG. 3 is a side view representation of a collection of scanplanes that are separated by approximately 7.5 degrees from each other.
Figure 4:
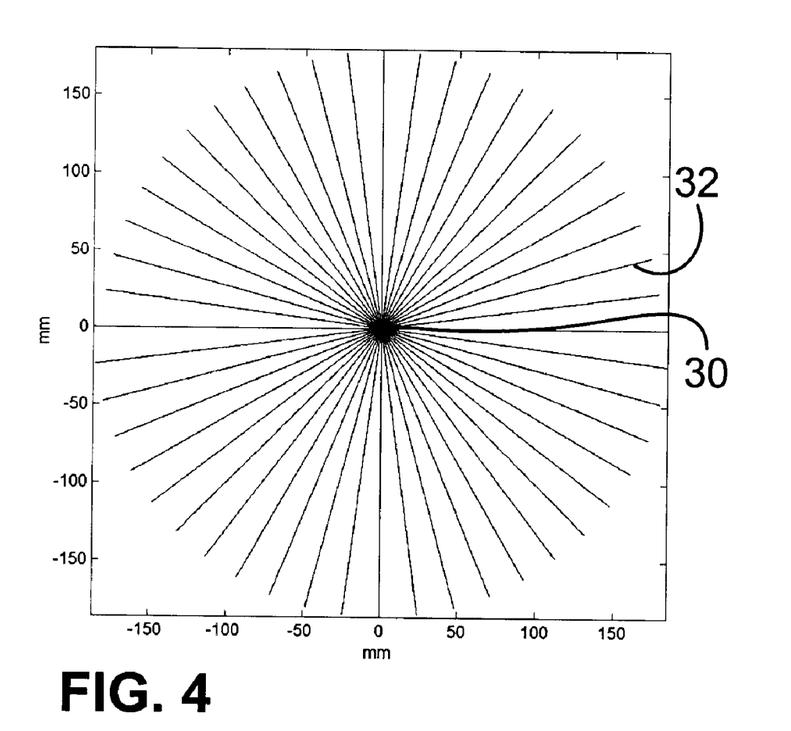
FIG. 4 is a top view representation of a collection of planes, each rotated 7.5 degrees from each other.

After a plane of scanlines is transmitted, the transceiver rotational angle $\theta$ is incremented slightly and another plane of pulse-echo signals are transmitted and received. This process is repeated as desired, producing a series of scanplanes in which each plane will be slightly rotated from the prior plane. As shown in FIG. 3, in the preferred embodiment each scanplane 32 is transmitted, received, and displayed into a twenty-four plane array, with approximately 7.5° separating each scanplane from its nearest neighbors. As illustrated in FIG. 3, the tilt angle $\phi$ sweeps through angles between −60° and 60° for a total of 120°. FIG. 4 presents a top view of twenty-four plane array.

As the scanlines are transmitted and received, the returning echoes are changed into analog electrical signals by a transducer, converted to digital signals by an analog-to-digital converter, and conveyed to the digital signal processor of the computer system for analysis to determine the locations of the bladder walls. The computer system itself is not depicted, but includes a microprocessor and a RAM, hard-drive, optical drive, or other memory for storing processing instructions and data generated by the transceiver 10.

Figure 5:
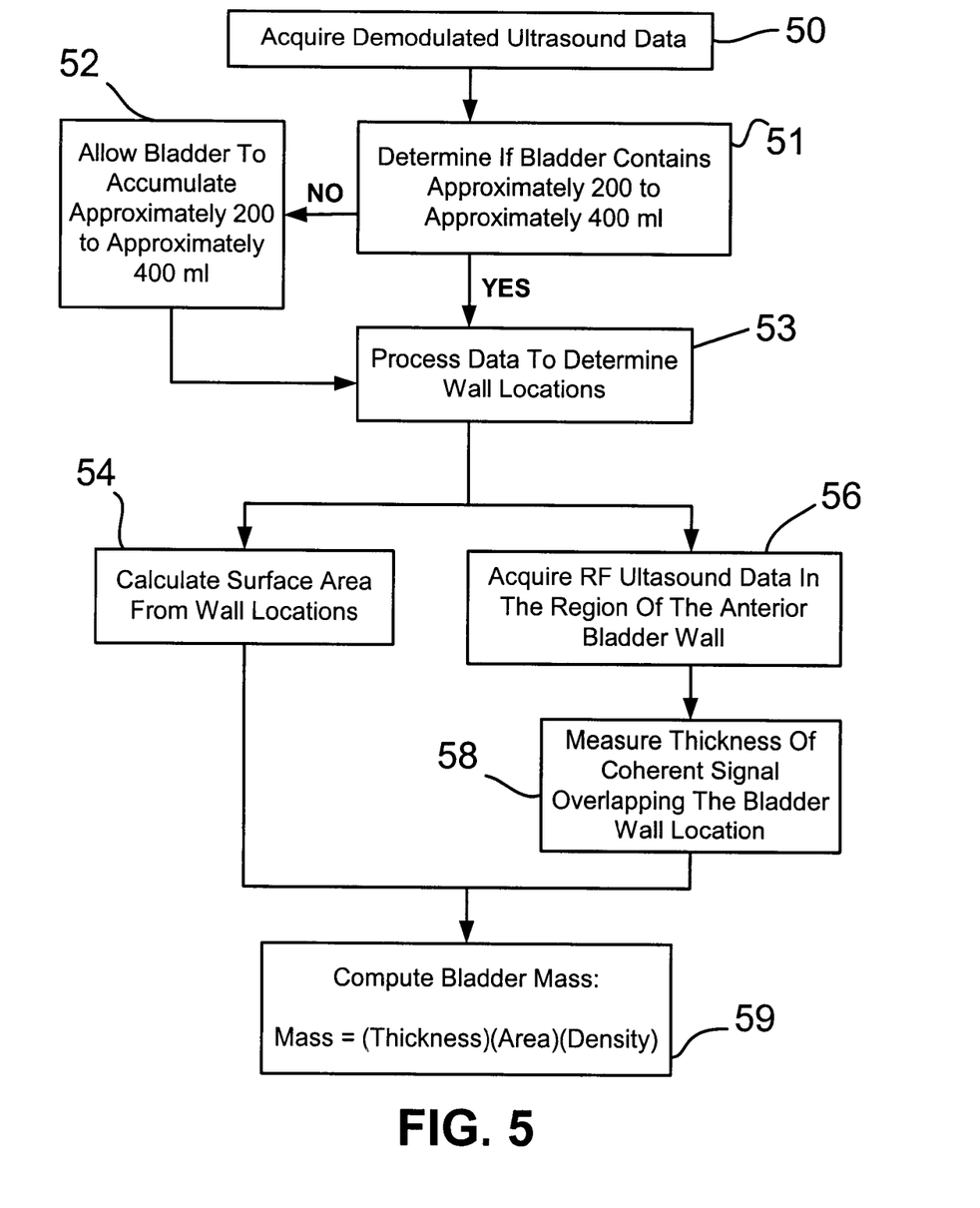
FIG. 5 is an algorithm for measuring bladder thickness and mass.

Once the wall locations are identified, the wall locations, demodulated magnitude data, and a subset of quadrature amplitude demodulated signal in the region of the anterior bladder wall are directed to the microprocessor for further analysis according to the algorithm illustrated in FIG. 5 for the preferred emobodiment of the invention. First, ultrasound data is acquired relative to the bladder, as shown in the first block 50. In general, bladder-specific data can be acquired by a user who manipulates the transceiver 10 while viewing the received data on a display screen and then positioning the transceiver 10 as necessary so that the bladder is sufficiently within the field of view of the cone as depicted in FIG. 3.

After obtaining ultrasound bladder data, the ultrasound data is processed to determine if the bladder contains approximately 200 to approximately 400 ml, as shown in the second block 51. If "No", then the bladder is allowed to accumulate approximately 200 to approximately 400 ml, as shown in the third block 52, or, if "Yes, meaning the bladder already contains the preferred approximate 200–400 ml volume, then the locations of the bladder walls, as shown in the fourth block 53, may be undertaken. The determination of organ wall locations and other such exterior boundaries within an ultrasound scan is within the capability of ultrasound devices presently on the market. In general, however, the process determines the length of a scanline from the transceiver dome to the bladder wall. The data, including wall locations, is stored in the computer memory.

Once the full cone of ultrasound magnitude data has been scanned and wall locations have been determined by the digital signal processor, the microprocessor further analyzes the data to correct any misdetection in wall location and to determine bladder volume. Two specific techniques for doing so are disclosed in detail in U.S. Pat. No. 4,926,871 to Ganguly et al and U.S. Pat. No. 5,235,985 to McMorrow et al, which are incorporated by reference. These patents provide detailed explanations for non-invasively transmitting, receiving and processing ultrasound signals relative to the bladder, and then for calculating bladder volume.

Using the methodology provided by the '871 and '985 patents, the data is used to determine whether or not the bladder volume is with a range of approximately 200 to approximately 400 ml. If the bladder volume is within that range, the ultrasound data is used to determine the actual surface area from the wall locations, as indicated in the fifth block 54. The surface area calculation is explained in greater detail below. While calculating the surface area in the fifth block 54, reflected RF ultrasound waves are received from the anterior bladder wall, as indicated in the sixth block 56. Although these tasks are preferably conducted in parallel, they may alternatively be processed in series. Thereafter, as shown in the seventh block 58, the bladder wall thickness is determined from the coherent signals that overlap at the wall locations. The determination of bladder wall thickness is explained in greater detail below. Finally, as shown in the seventh block 58, the bladder mass is computed as a product of thickness, area, and bladder density.

The volume restriction indicated in the previous paragraph is included as the range of bladder volumes that allow for an optimal measurement of the bladder mass. The mass calculation may be performed at a volume not in this range, but will result in a less accurate measurement. For example, bladder volumes less than 200 ml and greater than 400 ml can be measured, but with less accuracy. For volumes substantially greater than 400 ml, for example bladder volumes of 1000 ml to multi-liters, the invention will utilize scanlines greater than 20 cm to accommodate the larger bladder sizes. The invention may be applied to measure the thicknesses and masses of internal organs of human and animals. The length of the scanlines are adjusted to match the dimension of the internal organ scanned.

Surface area determination. The surface area measurement of fifth block 54 is performed by integrating the area of interpolating surface patch functions defined by the wall locations. The mathematical calculations are provided below in greater detail.

The surface of the bladder is defined to be S. This surface corresponds to the actual surface of the bladder determined by analysis of the wall locations of the bladder. Since this shape is not known in advance, modeling the bladder as a sphere or an ellipsoid provides only a crude approximation of the surface. Instead, the surface S is defined as a construction of a series of individual surface patches $s_{ij}$, where i and j count through the latitude and longitude components of the surface, similar to the division of the Earth's surface into lines of latitude and longitude. The area of the bladder surface, S, is defined as the sum of all the individual surface patches, $S=\Sigma s_{ij}$.

Figure 6:
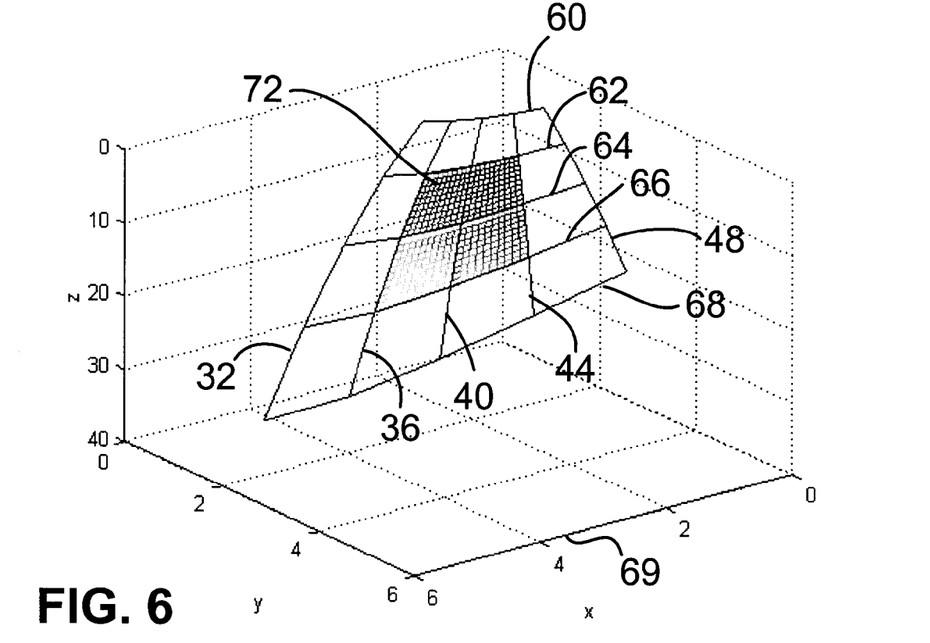
FIG. 6 is a representation of four surface patch elements, each constructed from the sixteen neighboring points that surround the patch.

As depicted in three dimensions in FIG. 6, by way of example, five scanplanes 32–48 are seen transmitted substantially longitudinally across a subserosal wall location 72 referenced to a tri-axis plotting grid 69. The five scanplanes include the first scanplane 32, a second scanplane 36, a third scanplane 40, a fourth scanplane 44, and a fifth scanplane 48. The scanplanes are represented in the preceeding formulas as subscripted variable j. Substantially normal to the five longitudinal scanplanes are five latitudinal integration lines 60–68 that include a first integration line 60, a second integration line 62, a third integration line 64, a fourth integration line 66, and a fifth integration line 68. The integration lines are represented in the preceeding formulas as subscripted variable i.

By way of example, four surface patch functions are highlighted in FIG. 6 as the subserosal wall location 72. The i and j subscripts mentioned previously correspond to indices for the lines of latitude and longitude of the bladder surface. For the purposes of this discussion, i will correspond to lines of longitude and j will correspond to lines of latitude although it should be noted the meanings of i and j can be interchanged with a mathematically equivalent result. Using the scanplane and integration line definitions provided in FIG. 6, the four surface patch functions are identified, in the clockwise direction starting in the upper left, as $s_{36,62}$, $s_{40,62}$, $s_{40,64}$, and $s_{36,64}$.

The surface patches are defined as functions of the patch coordinates, $s_{ij}(u,v)$. The patch coordinates u and v, are defined such that $0 \leq u, v < 1$ where 0 represents the starting latitude or longitude coordinate (the i and j locations), and 1 represents the next latitude or longitude coordinate (the i+1 and j+1 locations). The surface function could also be expressed in Cartesian coordinates where $s_{ij}(u,v) = x_{ij}(u,v)i + y_{ij}(u,v)j + z_{ij}(u,v)k$ where i, j, k, are unit vectors in the x-, y-, and z- directions respectively. In vector form, the definition of a surface patch function is given in Equation 1.

$$s_{i,j}(u, v) = \begin{bmatrix} x_{i,j}(u, v) \\ y_{i,j}(u, v) \\ z_{i,j}(u, v) \end{bmatrix} \qquad \text{Equation 1.}$$

With the definitions of surface patch functions complete, attention can turn to the surface area calculation represented in the fifth block 54 of FIG. 5. The surface area of S, A(S), can be defined as the integration of an area element over the surface S, as shown in Equation 2. Since S is composed of a number of the patch surface functions, the calculation for the area of the surface S can be rewritten as the sum of the areas of the individual surface patch functions as in Equation 3.

$$A(S) = \int_S dA \qquad \text{Equation 2.}$$

$$A(S) = \sum_{i,j} A(s_{i,j}) \qquad \text{Equation 3.}$$

Similarly to Equation 2 for the entire surface, the area of the surface patch is the integration of an area element over the surface patch, shown in Equation 4. The integration over the surface patch function can be simplified computationally by transforming the integration over the surface to a double integration over the patch coordinates u and v. The transformation between the surface integration and the patch coordinate integration is shown in Equation 5.

$$A(s_{i,j}) = \int_{s_{i,j}} dA_{i,j} \qquad \text{Equation 4.}$$

$$\int_{s_{i,j}} dA_{i,j} = \int_{u=0}^{1} \int_{v=0}^{1} \left| \frac{\partial s_{i,j}}{\partial u} \times \frac{\partial s_{i,j}}{\partial v} \right| dv\, du \qquad \text{Equation 5.}$$

By substituting Equation 5 into Equation 4, and Equation 4 into Equation 3, the area for the entire surface can be calculated. The result of these substitutions is shown in Equation 6.

$$A(S) = \sum_{i,j} \int_u \int_v \left| \frac{\partial s_{i,j}}{\partial u} \times \frac{\partial s_{i,j}}{\partial v} \right| dv\, du \qquad \text{Equation 6.}$$

The surface patch function may be any function that is continuous in its first derivatives. In the embodiment shown, a cubic B-spline interpolating function is used for the interpolating surface patch function although any surface function may be used. This interpolating function is applied to each of the Cartesian coordinate functions shown in Equation 1. The interpolating equation for the x-coordinate of the $s_{ij}$ patch function is given in Equation 7. Similar calculations are performed for the $y_{ij}$ and $z_{ij}$ components of the surface patch function.

$$x_{i,j}(u,v) = u M_b X_{i,j} M_b^t v^t \qquad \text{Equation 7.}$$

where t denotes matrix and vector transpose, $$u = \begin{bmatrix} u^3 \\ u^2 \\ u \\ 1 \end{bmatrix}, \quad v = \begin{bmatrix} v^3 \\ v^2 \\ v \\ 1 \end{bmatrix},$$

$$M_b = \begin{bmatrix} -1 & 3 & -3 & 1 \\ 3 & -6 & 3 & 0 \\ -3 & 0 & 3 & 0 \\ 1 & 4 & 1 & 0 \end{bmatrix}, \text{ and}$$

$$X_{i,j} = \begin{bmatrix} x_{i-1,j-1} & x_{i-1,j} & x_{i-1,j+1} & x_{i-1,j+2} \\ x_{i,j-1} & x_{i,j} & x_{i,j+1} & x_{i,j+2} \\ x_{i+1,j-1} & x_{i+1,j} & x_{i+1,j+1} & x_{i+1,j+2} \\ x_{i+2,j-1} & x_{i+2,j} & x_{i+2,j+1} & x_{i+2,j+2} \end{bmatrix}$$

Since the interpolating functions for each of the patch functions is a cubic surface, the integration may be performed exactly using a quadrature formula. The formula used in this application is shown in Equation 8.

$$A(s_{i,j}) = \sum_{i,j} \frac{1}{4} \begin{pmatrix} \left| \frac{\partial s_{i,j}}{\partial u} \times \frac{\partial s_{i,j}}{\partial v} \right|_{u=\frac{3-\sqrt{3}}{6}, v=\frac{3-\sqrt{3}}{6}} + \\ \left| \frac{\partial s_{i,j}}{\partial u} \times \frac{\partial s_{i,j}}{\partial v} \right|_{u=\frac{3-\sqrt{3}}{6}, v=\frac{3+\sqrt{3}}{6}} + \\ \left| \frac{\partial s_{i,j}}{\partial u} \times \frac{\partial s_{i,j}}{\partial v} \right|_{u=\frac{3+\sqrt{3}}{6}, v=\frac{3-\sqrt{3}}{6}} + \\ \left| \frac{\partial s_{i,j}}{\partial u} \times \frac{\partial s_{i,j}}{\partial v} \right|_{u=\frac{3+\sqrt{3}}{6}, v=\frac{3+\sqrt{3}}{6}} \end{pmatrix} \qquad \text{Equation 8.}$$

Recalling the fact that $s_{ij}(u,v)$ is defined as a vector function in Cartesian coordinates (Equation 1), the norm of the cross product of the partial derivatives can be written as follows:

$$\left| \frac{\partial s_{i,j}}{\partial u} \times \frac{\partial s_{i,j}}{\partial u} \right| = \sqrt{ \begin{array}{l} \left( \frac{\partial y_{i,j}}{\partial u} \frac{\partial z_{i,j}}{\partial v} - \frac{\partial z_{i,j}}{\partial u} \frac{\partial y_{i,j}}{\partial v} \right)^2 + \\ \left( \frac{\partial z_{i,j}}{\partial u} \frac{\partial x_{i,j}}{\partial v} - \frac{\partial z_{i,j}}{\partial u} \frac{\partial x_{i,j}}{\partial v} \right)^2 + \\ \left( \frac{\partial x_{i,j}}{\partial u} \frac{\partial y_{i,j}}{\partial v} - \frac{\partial y_{i,j}}{\partial u} \frac{\partial x_{i,j}}{\partial v} \right)^2 \end{array} } \qquad \text{Equation 9.}$$

When the physical x-, y-, and z- locations are used in the interpolating function, the surface are will be calculated in the square of the units of x, y, and z. At this point the calculation in the fifth block 54 of FIG. 5 is complete.

Wall thickness determination. The second component to the mass calculation is a measurement of the thickness of the bladder muscle wall. This thickness is defined to be the normal thickness between the subserosal and submucosal surfaces of the bladder wall.

The wall thickness is calculated from the fractal dimension of the RF signal in the region of the wall thickness. The fractal dimension increases due to the multiplicity of interface reflections through the bladder muscle. The increase and decrease of fractal dimension through the bladder muscle wall can be modeled as a parabola where the fractal dimension is a function of the depth in the region of the bladder wall. The thickness of the bladder is then determined to be the region of the parabola model that is at least 97% of the maximal value of the fractal dimension. The calculations are reviewed below in Equation 10.

$$fd_r = \frac{\log\left( \frac{\max(RF_{r=r-w/2, r+w/2}) - \min(RF_{r=r-w/2, r+w/2}) + w}{w} \right)}{\log\left(\frac{n}{w}\right)} \qquad \text{Equation 10.}$$

The fractal dimension calculation corresponds to the fourth block 56 of FIG. 5. The fractal dimension is calculated for a window of length w. In the current embodiment the value of w is 5, the number of sample points along a scanline, although that value can be varied. The fractal dimension is calculated from the difference between the maximum RF signal value in the window centered at a given depth, r, and the minimum of that same window. The length of the window, w, is added to this difference, and the result is then normalized with the length of the window. The logarithm of that result is then divided by the logarithm of the ratio of the total number of samples in a scanline, n, to the length of the window. The calculation of the fractal dimension at each depth along a scanline is shown in Equation 10. This fractal dimension measure is calculated for the central n-w samples in a scanline.

After the measurements of the fractal dimension have been calculated based on the ultrasound signal, the thickness of the bladder wall may be calculated. The following calculations correspond to the seventh block 58 of FIG. 5.

The fractal dimension, fd, of the RF signal in the region of the bladder muscle wall is then modeled as a parabolic equation as a function of depth, r. The model of the equation for a single depth point is given in Equation 11. In that equation, there are 3 parameters (a, b, and c) that define the parabola with the depth along a scanline r, and the addition of a random element $\epsilon$. The subscript i indicates a specific value of r,fd, and $\epsilon$.

$$fd_i = ar_i^2 + br_i + c + \epsilon_i \qquad \text{Equation 11.}$$

An equation of the form in Equation 11 is obtained for each depth point in the region of the wall. The number of observations is variable and depends on the thickness of the bladder wall as observed by the ultrasound signal. Assuming a set of n observations, the subscript i would count the observations from 1 to n. The set of n equations of the form in Equation 11 may be compressed into a matrix equation given in Equation 12. Each row of the fd, and $\epsilon$, and the X matrix correspond to one of the n observations. The parabola parameters of Equation 11 are collected in the vector $\beta$.

$$fd = X\beta + \varepsilon \qquad \text{Equation 12.}$$

where $$fd = \begin{bmatrix} fd_1 \\ fd_2 \\ \vdots \\ fd_n \end{bmatrix}, X = \begin{bmatrix} r_1^2 & r_1 & 1 \\ r_2^2 & r_2 & 1 \\ \vdots & \vdots & \vdots \\ r_n^2 & r_n & 1 \end{bmatrix},$$

$$\beta = \begin{bmatrix} a \\ b \\ c \end{bmatrix}, \text{ and } \varepsilon = \begin{bmatrix} \varepsilon_1 \\ \varepsilon_2 \\ \vdots \\ \varepsilon_n \end{bmatrix}$$

The next step is to estimate the values of the parameters of the parabola in the set of n equations of the form in Equation 11 or in the matrix Equation 12 based on the set of observations. A least-squares estimation of the parameters is used, and the calculation for these estimates is shown in Equation 13. In Equation 13, the t superscript indicates matrix transpose, and the −1 superscript indicates the matrix inverse. Parameters with hats (^) indicate that the value is the least-squares estimate of those parameters.

$$\hat{\beta} = (X^t X)^{-1} X^t fd \qquad \text{Equation 13.}$$

The estimates of the parabola parameters ($\hat{\beta} = \lfloor \hat{a} \hat{b} \hat{c} \rfloor^t$) can be substituted into the parabola model to calculate the estimated fractal dimension at each depth r, as shown in Equation 14. The location of the maximum fractal dimension can be determined by setting the first derivative of the parabola model to equal 0 (Equation 15) and solving for r. The location where the fractal dimension is maximal is given in Equation 16.

$$\hat{fd}(r) = \hat{a}r^2 + \hat{b}r + \hat{c} \qquad \text{Equation 14.}$$

$$\frac{d\hat{fd}(r)}{dr} = 2\hat{a}r + \hat{b} = 0 \qquad \text{Equation 15.}$$

$$r_{fd_{\max}} = -\frac{\hat{b}}{2\hat{a}} \qquad \text{Equation 16.}$$

To determine the maximal fractal dimension as defined by the parabolic model, simply substitute Equation 16 into Equation 14 and solve for $fd_{max}$. The resulting value is shown in Equation 17.

$$\hat{fd}_{\max} = \frac{-\hat{b}^2 + 4\hat{c}}{4\hat{a}} \qquad \text{Equation 17.}$$

To determine the locations where the fractal dimension is 97% of the maximum value, multiply Equation 17 by 0.97, substitute the result into Equation 14 and solve for r using the quadratic formula. The locations where the fractal dimension is 97% of the maximum value, $r_{97\%}$, are given in Equation 18.

$$r_{97\%} = \frac{-\hat{b} \pm \sqrt{\hat{b}^2 - 4\hat{a}\left(\hat{c} + 0.97 \frac{\hat{b}^2 + 4\hat{c}}{4\hat{a}}\right)}}{2\hat{a}} \qquad \text{Equation 18.}$$

Two values for $r_{97\%}$ will be calculated from Equation 18. The difference between those two values will identify the thickness of the bladder muscle wall along the given scanline. Since these scanlines may or may not be perpendicular to the bladder muscle surface and bladder wall thickness must be measured along a line perpendicular to the bladder surface, a collection of these measurements are combined to determine the actual thickness of the bladder wall.

Figure 7:
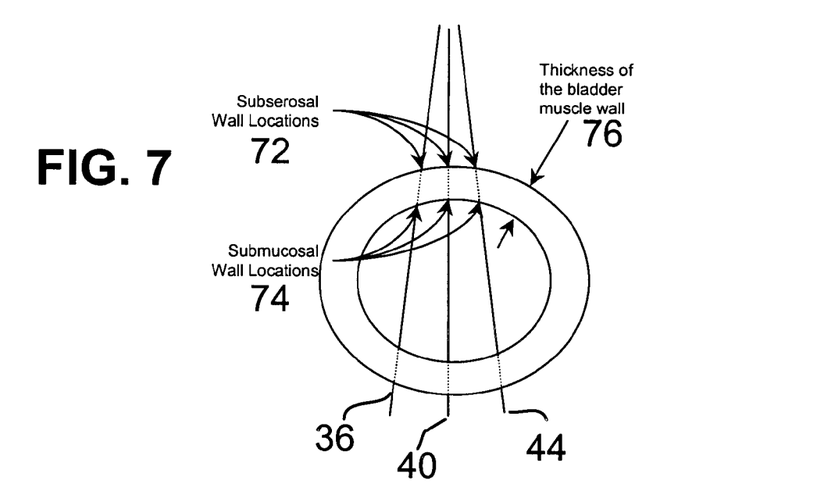
FIG. 7 is a representation of three scanlines passing through the subserosal and submucosal wall locations of the bladder.

These measurements could be made at any surface of the bladder muscle wall. In FIG. 7, three scanlines are shown to cross the bladder muscle in two locations: the anterior wall closest to the transducer, and the posterior wall furthest from the transducer. The plarabolic model described previously can be applied twice on each to determine the thickness of both the anterior and posterior wall. The maximum and minimum and mean values of these thicknesses are used in the mass calculation and historical tracking of data. In the embodiment shown, this final thickness determination marks the end of the process identified in the seventh block 58 of FIG. 5.

The three scanplanes of FIG. 7 are the second scanplane 36, the third scanplane 40, and the fourth scanplane 44. The dotted portion of the lines represents the portion of the scanplanes that passes through the bladder muscle wall. The second 36, the third 40, and fourth 44 scanlines are shown transmitting through the subserosal wall location 72 and submucosal wall location 74. The maximum and minimum and mean values of these thicknesses are used in the mass calculation and historical tracking of data. In the preferred embodiment, the bladder is assumed to have a uniform wall thickness, so that a mean wall thickness value is derived from the scanned data and used for the bladder mass determination. Only three scanlines are shown in a plane, each separated by 7.5 degrees from each other. Both the number of scanlines in the plane and the angles separating each scanline within a plane may be varied.

Bladder mass determination. Once the thickness and the surface area have been measured, the mass of the bladder may be calculated. The volume of muscle tissue is assumed to be the surface area times the wall thickness, where the assumption is based on a uniform wall thickness at all points around the bladder. The mass is then the product of the volume of muscle tissue, the specific gravity of the bladder muscle tissue and the density of water. The specific gravity of bladder muscle is a known value readily available in medical reference texts. In the embodiment shown, this mass calculation corresponds to the eighth block 59 of FIG. 5.

The methods to obtain the wall-thickness data and the mass data via downloaded digital signals can be configured by the microprocessor system for remote operation via the Internet web-based system. The Internet web-based system ("System For Remote Evaluation Of Ultrasound Information Obtained By A Program Application-Specific Data Collection Device") is described in patent application Ser. No. 09/620,766, herein incorporated by reference. The internet web-based system has multiple programs that collect, analyze, and store organ thickness and organ mass determinations. The alternate embodiment thus provides an ability to measure the rate at which internal organs undergo hypertrophy with time and permits disease tracking, disease progression, and provides educational instructions to patients.

While the preferred embodiment of the invention has been illustrated and described, as noted above, many changes can be made without departing from the spirit and scope of the invention. Accordingly, the scope of the invention is not limited by the disclosure of the preferred embodiment.

What is claimed is:

1. A method to determine bladder wall mass, the method comprising:

positioning an ultrasound transceiver exterior to a patient such that at least a portion of the bladder is within a field of view of the transceiver, the ultrasound transceiver configured to send radio frequency ultrasound pulses and to receive echoes of the radio frequency ultrasound pulses;

sending the radio frequency ultrasound pulses from the ultrasound transceiver to a bladder wall surface;

receiving echoes of the radio frequency ultrasound pulses reflected from the bladder wall surface;

calculating the surface area of the bladder based on the received ultrasound echoes:

calculating the thickness of at least a portion of the bladder wall based on the received ultrasound echoes; and calculating the mass of the bladder wall as a function of the calculated surface area and thickness, wherein the area of the bladder wall is defined to be S, and comprises a plurality of surface patches, $s_{ij}$, where i and j are latitude and longitude components, such that the area of S is the sum of the plurality of patches, $S = \Sigma s_{ij}$.

2. The method of claim 1, wherein the area of the bladder wall is determined for bladders containing approximately 200 ml to approximately 400 ml.

3. The method of claim 1, wherein the area of the bladder wall is determined for bladders containing approximately 0 ml to approximately 200 ml.

4. The method of claim 1, wherein the area of the bladder wall is determined for bladders containing approximately 400 ml to approximately 1000 ml.

5. The method of claim 1, wherein the each surface patch $S_{ij}$ is further defined by a vector $s_{ij}(u,v)=x_{ij}(u,v)i+y_{ij}(u,v)j+z_{ij}(u,v)k$, where i, j, k, are unit vectors in the x-, y-, and z- directions respectively, and u and v are surface patch coordinates.

6. The method of claim 1, wherein the thickness separating the inner and outer wall regions is further determined from the relationship $$fd_r = \frac{\log\left(\frac{\max(RF_{r=r-w/2, r+w/2}) - \min(RF_{r=r-w/2, r+w/2}) + w}{w}\right)}{\log\left(\frac{n}{w}\right)}$$

wherein the terms max $(RF_{r=r-w/2, r+w/2})$ and min $(RF_{r=r-w/2, r+w/2})+w$ refer to the maximum and minimum radio frequency (RF) value for a window of length w, centered at a given depth, r, along a scanline of a given number of samples, n,, such that the fractal dimension is calculated from the difference between the maximum radio frequency (RF) signal value in the window centered at a given depth, r, then normalized with a total number of samples in a scanline, n.

7. The method of claim 6, where the thickness separating the inner and outer wall regions fdr is adjusted by a parabolic function of the form is determined from the relationship $fd_i = ar_i^2 + br_i + c + \epsilon_i$, where there are 3 parameters (a, b, and c) that define a parabola function with the depth along a scanline r, and the addition of a random element $\epsilon$, wherein the subscript i indicates a specific value of r, fd, and $\epsilon$.

8. The method of claim 7, where the parabola function is at least 97% of the maximal value of a fractal dimension is determined from the relationship $$r_{97\%} = \frac{-\hat{b} \pm \sqrt{\hat{b}^2 - 4\hat{a}\left(\hat{c} + 0.97\frac{\hat{b}^2 + 4\hat{c}}{4\hat{a}}\right)}}{2\hat{a}},$$

where the parameters with hats (^) indicate that the value is the least-squares estimate of those parameters.

9. A system for determining the mass of an internal organ, the system comprising:

a transceiver having a display and configured to deliver radio frequency ultrasound pulses in a plurality of scanplanes to the organ of a patient, each scanplane separated by approximately 7.5 degrees and formed by a plurality of scanlines, the transceiver further configured to receive pulses reflected from the organ, and process the received echoes to determine the latitudinal and longitudinal components of the echoes; and a computer system in communication with the transceiver, the computer system having a microprocessor and a memory configured to present the graphic image of each scanplane in two-dimensions and the plurality of scanplanes in three-dimensions, the memory further containing stored programming instructions operable by the microprocessor to determine the surface area of the organ from the latitudinal and longitudinal components of the echoes, the thickness of the organ based on the echoes received by the transceiver, and the mass of the organ as a function of organ thickness and area.

10. The system of claim 9, wherein the organ is a bladder.

11. The system of claim 9, wherein the stored programming instructions in the memory further comprise a plurality of equations to calculate bladder wall surface area and bladder wall thickness at one or more of anterior, posterior, or lateral locations of the bladder wall.

12. The system of claim 11, wherein the plurality of equations to measure bladder wall surface area include $$s_{i,j}(u, v) = \begin{bmatrix} x_{i,j}(u, v) \\ y_{i,j}(u, v) \\ z_{i,j}(u, v) \end{bmatrix}, \quad A(S) = \sum_{i,j} A(s_{i,j}),$$

$$A(s_{i,j}) =$$

$$\sum_{i,j} \frac{1}{4} \left( \left| \frac{\partial s_{i,j}}{\partial u} \times \frac{\partial s_{i,j}}{\partial v} \right|_{u=\frac{3-\sqrt{3}}{6}, v=\frac{3-\sqrt{3}}{6}} + \left| \frac{\partial s_{i,j}}{\partial u} \times \frac{\partial s_{i,j}}{\partial v} \right|_{u=\frac{3-\sqrt{3}}{6}, v=\frac{3+\sqrt{3}}{6}} + \right.$$

$$\left| \frac{\partial s_{i,j}}{\partial u} \times \frac{\partial s_{i,j}}{\partial v} \right|_{u=\frac{3+\sqrt{3}}{6}, v=\frac{3-\sqrt{3}}{6}} +$$

$$\left. \left| \frac{\partial s_{i,j}}{\partial u} \times \frac{\partial s_{i,j}}{\partial v} \right|_{u=\frac{3+\sqrt{3}}{6}, v=\frac{3+\sqrt{3}}{6}} \right), \text{ and}$$

$$\left| \frac{\partial s_{i,j}}{\partial u} \times \frac{\partial s_{i,j}}{\partial u} \right| =$$

$$\sqrt{\left(\frac{\partial y_{i,j}}{\partial u}\frac{\partial z_{i,j}}{\partial v} - \frac{\partial z_{i,j}}{\partial u}\frac{\partial y_{i,j}}{\partial v}\right)^2 + \left(\frac{\partial z_{i,j}}{\partial u}\frac{\partial x_{i,j}}{\partial v} - \frac{\partial z_{i,j}}{\partial u}\frac{\partial x_{i,j}}{\partial v}\right)^2 + \left(\frac{\partial x_{i,j}}{\partial u}\frac{\partial y_{i,j}}{\partial v} - \frac{\partial y_{i,j}}{\partial u}\frac{\partial x_{i,j}}{\partial v}\right)^2}.$$

13. The system of claim 11, wherein the equations used to calculate bladder wall thickness include $$fd_r = \frac{\log\left(\frac{\max(RF_{r=r-w/2,r+w/2}) - \min(RF_{r=r-w/2,r+w/2}) + w}{w}\right)}{\log\left(\frac{n}{w}\right)},$$

and $$\text{fd}_i = ar_i^2 + br_{i+c+\epsilon_i},$$

and $$r_{97\%} = \frac{-\hat{b} \pm \sqrt{\hat{b}^2 - 4\hat{a}\left(\hat{c} + 0.97\frac{\hat{b}^2 + 4\hat{c}}{4\hat{a}}\right)}}{2\hat{a}}.$$

14. The system of claim 9, wherein the computer system is configured for remote operation via an Internet web-based system, the internet web-based system having a plurality of programs that collect, analyze, and store organ thickness and organ mass determinations, such that the rate at which internal organs undergo hypertrophy may be determined.

15. The system of claim 14, wherein the plurality of programs further include instructions to permit disease tracking, disease progression, and provides educational instructions to patients.

16. A system for determining the mass of an internal organ, the system comprising:
a transceiver configured to deliver radio frequency ultrasound pulses in a plurality of scanplanes to the organ of a patient and receive echoes of the pulses reflected from the organ and process the received echoes to determine the latitudinal and longitudinal components of the echoes; and
a means for determining the surface area of the organ from the latitudinal and longitudinal components of the echoes and the thickness of the organ based on the echoes received by the transceiver, and further to calculate the mass of the organ as a function of the organ thickness and area.

17. The system of claim 16, wherein the transceiver further delivers and receives the radio frequency ultrasound pulses adjusted for the anatomy of male and female patients.

18. The system of claim 16, wherein the means for determining the surface area of the organ include a first plurality of equations to analyze the echoes received by the transceiver, the first plurality of equations including $$s_{i,j}(u, v) = \begin{bmatrix} x_{i,j}(u, v) \\ y_{i,j}(u, v) \\ z_{i,j}(u, v) \end{bmatrix}; \quad A(S) = \sum_{i,j} A(s_{i,j});$$

$$A(s_{i,j}) =$$

$$\sum_{i,j} \frac{1}{4} \left( \left| \frac{\partial s_{i,j}}{\partial u} \times \frac{\partial s_{i,j}}{\partial v} \right|_{u=\frac{3-\sqrt{3}}{6}, v=\frac{3-\sqrt{3}}{6}} + \left| \frac{\partial s_{i,j}}{\partial u} \times \frac{\partial s_{i,j}}{\partial v} \right|_{u=\frac{3-\sqrt{3}}{6}, v=\frac{3+\sqrt{3}}{6}} + \right.$$

$$\left| \frac{\partial s_{i,j}}{\partial u} \times \frac{\partial s_{i,j}}{\partial v} \right|_{u=\frac{3+\sqrt{3}}{6}, v=\frac{3-\sqrt{3}}{6}} +$$

$$\left. \left| \frac{\partial s_{i,j}}{\partial u} \times \frac{\partial s_{i,j}}{\partial v} \right|_{u=\frac{3+\sqrt{3}}{6}, v=\frac{3+\sqrt{3}}{6}} \right); \text{ and}$$

$$\left| \frac{\partial s_{i,j}}{\partial u} \times \frac{\partial s_{i,j}}{\partial u} \right| =$$

$$\sqrt{\left(\frac{\partial y_{i,j}}{\partial u}\frac{\partial z_{i,j}}{\partial v} - \frac{\partial z_{i,j}}{\partial u}\frac{\partial y_{i,j}}{\partial v}\right)^2 + \left(\frac{\partial z_{i,j}}{\partial u}\frac{\partial x_{i,j}}{\partial v} - \frac{\partial z_{i,j}}{\partial u}\frac{\partial x_{i,j}}{\partial v}\right)^2 + \left(\frac{\partial x_{i,j}}{\partial u}\frac{\partial y_{i,j}}{\partial v} - \frac{\partial y_{i,j}}{\partial u}\frac{\partial x_{i,j}}{\partial v}\right)^2}.$$

19. The system of claim 16, wherein the means to determine the thickness of the organ include a second plurality of equations to analyze the echoes received by the transceiver, the second plurality of equations including $$fd_r = \frac{\log\left(\frac{\max(RF_{r=r-w/2,r+w/2}) - \min(RF_{r=r-w/2,r+w/2}) + w}{w}\right)}{\log\left(\frac{n}{w}\right)},$$

$$\text{fd}_i = ar_i^2 + br_i + c + \epsilon_i,$$

and $$r_{97\%} = \frac{-\hat{b} \pm \sqrt{\hat{b}^2 - 4\hat{a}\left(\hat{c} + 0.97\frac{\hat{b}^2 + 4\hat{c}}{4\hat{a}}\right)}}{2\hat{a}}.$$

20. A system for determining the wall thickness of an internal organ, the system comprising:
a transceiver configured to deliver radio frequency ultrasound pulses in a plurality of scanplanes to the organ of a patient and receive echoes of the pulses reflected from the organ and process the received echoes to determine the latitudinal and longitudinal components of the echoes; and
a means for determining the thickness of the organ from the latitudinal and longitudinal components of the echoes based on the echoes received by the transceiver.

21. The system of claim 20, wherein the means for determining the thickness of the organ include a plurality of equations to analyze the echoes received by the transceiver, the plurality of equations including $$fd_r = \frac{\log\left(\frac{\max(RF_{r=r-w/2,r+w/2}) - \min(RF_{r=r-w/2,r+w/2}) + w}{w}\right)}{\log\left(\frac{n}{w}\right)};$$

$$fd_i = ar_1^2 + br_i + c + \varepsilon_i; \qquad fd = X\beta + \varepsilon$$

where $fd = \begin{bmatrix} fd_1 \\ fd_2 \\ \vdots \\ fd_n \end{bmatrix}$, $X = \begin{bmatrix} r_1^2 & r_1 & 1 \\ r_2^2 & r_2 & 1 \\ \vdots & \vdots & \vdots \\ r_n^2 & r_n & 1 \end{bmatrix}$, $\beta = \begin{bmatrix} a \\ b \\ c \end{bmatrix}$, $\varepsilon = \begin{bmatrix} \varepsilon_1 \\ \varepsilon_2 \\ \vdots \\ \varepsilon_n \end{bmatrix}$;

$$\hat{\beta} = (X^t X)^{-1} X^t fd; \quad f\hat{d}(r) = \hat{a}r^2 + \hat{b}r + c;$$

$$\frac{d f\hat{d}(r)}{dr} = 2\hat{a}r + \hat{b} = 0;$$

$$r_{f\hat{d}_{\max}} = -\frac{\hat{b}}{2\hat{a}}; \quad f\hat{d}_{\max} = \frac{-\hat{b}^2 + 4\hat{c}}{4\hat{a}}; \quad \text{and}$$

$$r_{97\%} = \frac{-\hat{b} \pm \sqrt{\hat{b}^2 - 4\hat{a}\left(\hat{c} + 0.97 \frac{\hat{b}^2 + 4\hat{c}}{4\hat{a}}\right)}}{2\hat{a}}.$$

\* \* \* \* \*